United States Patent [19]

Wunderlich et al.

[11] Patent Number: 5,902,606
[45] Date of Patent: May 11, 1999

[54] SOLID AND LIQUID SOLUTIONS OF SPARINGLY WATER-SOLUBLE MEDICINAL SUBSTANCES

[75] Inventors: Jens-Christian Wunderlich, Heidelberg; Ursula Schick, Schriesheim; Jürgen Werry, Ludwigshafen; Jürgen Freidenreich, Schriesheim, all of Germany

[73] Assignee: Alfatec-Pharma GmbH, Heidelberg, Germany

[21] Appl. No.: 08/362,466

[22] PCT Filed: Jul. 5, 1993

[86] PCT No.: PCT/DE93/00592

§ 371 Date: Mar. 17, 1995

§ 102(e) Date: Mar. 17, 1995

[87] PCT Pub. No.: WO94/01090

PCT Pub. Date: Jan. 20, 1994

[30] Foreign Application Priority Data

Jul. 3, 1992 [DE] Germany ............................. 42 21 880

[51] Int. Cl.[6] ................ A61K 9/14; A61K 9/20
[52] U.S. Cl. ............... 424/464; 424/465; 424/489; 514/772.2; 514/772.3; 514/773; 514/774; 514/775; 514/776; 514/777; 514/778; 514/779; 514/782; 514/783

[58] Field of Search ..................... 424/464, 465, 424/489; 514/772.2, 772.3, 773, 774, 775, 776, 777, 778, 779, 782, 783

[56] References Cited

U.S. PATENT DOCUMENTS 5,080,907  1/1992  Iijima et al. ............................. 424/469

FOREIGN PATENT DOCUMENTS

B-36573/89  6/1989  Australia .
B-60239/90  8/1990  Australia .

*Primary Examiner*—Thurman K. Page
*Assistant Examiner*—James M. Spear
*Attorney, Agent, or Firm*—Burns, Doane, Swecker & Mathis L.L.P.

[57] ABSTRACT

Sparingly water-soluble active compounds, for example medicinal substances, are converted into the dissolved (molecularly disperse) state by dissolving them in a hydrophilic peptide having a molecular weight above 100 D, for example gelatin. The solubility both during storage and during use of the formulation by the user or patient is thereby ensured, without organic solvents or solubilizing agents which cause undesirable side effects being required.

50 Claims, No Drawings

SOLID AND LIQUID SOLUTIONS OF SPARINGLY WATER-SOLUBLE MEDICINAL SUBSTANCES

This application is a 371 of PCT/DE93/00592 filed Jul. 5, 1993.

The present invention relates to a formulation comprising sparingly water-soluble medicinal substances, which has a molecularly disperse distribution of the sparingly water-soluble medicinal substance in a hydrophilic peptide having a molecular weight above 100 D.

The invention furthermore relates to a process for the preparation of such formulations comprising sparingly water-soluble medicinal substances.

The invention also relates to pharmaceutical formulations which comprise such formulations of sparingly water-soluble medicinal substances.

The problem of imparting solubility to or solubilizing sparingly water-soluble substances is sufficiently known, for example, in pharmaceutical technology. The presence of the substance in the dissolved and non-dissociated state is an essential prerequisite for absorption of the substance in the organism. To remedy this problem, a number of possibilities exist:

Changes to the molecule itself include measures such as salt formation or introduction of a hydrophilic molecular radical. Although such interventions lead to compounds which have a better water-solubility, these are dissociated or changed in their original molecular structure.

The use of organic solvents, such as, for example, ethanol or polyethylene glycols, for example in liquid formulations, is not always desirable or promising bearing in mind that, on aqueous dilution in the physiological medium, the substances thus kept in solution may precipitate and are therefore not absorbable.

If surfactants are employed as solubilizing agents, or water-soluble complexes (for example cyclodextrin inclusion compounds) are prepared, possible undesirable side effects, such as, for example, the membrane-damaging cellular action of such substances, must be borne in mind.

Finally, the hydrotropic substances, such as urea or N-methylacetamide, may also be mentioned, but these have to be used in concentrations of 20–30% in order to obtain a true solution.

Summarizing, it can thus be said that the prior art to date offers no satisfactory solutions and in many cases adequate solubilization has still not been found for substances which present particular problems.

This fact means that medicinal formulations of sparingly water-soluble medicinal substances are to be evaluated critically in respect of their preparation and use in treatment.

The invention is therefore based on the object of converting sparingly water-soluble medicinal substances into a form such that the dissolved (molecularly disperse) state of the medicinal substance is ensured in a simple manner both during storage and during use of the formulation by the user or patient, without being associated directly with the presence of organic solvents or of solubilizing agents which cause undesirable side effects.

It is a particular object of the present invention to develop medicaments which comprise sparingly water-soluble medicinal substances and which avoid the disadvantages mentioned for the prior art and therefore improve the efficacy and bioavailability of such substances, in order to achieve an effective therapeutic utilization of such drugs.

This object is achieved by a formulation comprising sparingly water-soluble medicinal substances, which has a molecularly disperse distribution of the sparingly water-soluble medicinal substance in a hydrophilic peptide having a molecular weight above 100 D.

This object is furthermore achieved by a process for the preparation of such formulations comprising sparingly water-soluble medicinal substances as claimed in claim 24. Embodiments of the formulations according to the invention and of the process for their preparation are mentioned and claimed in the subclaims.

Finally, this object is achieved by pharmaceutical formulations which comprise such formulations of sparingly water-soluble medicinal substances.

The present invention is thus based on the completely surprising finding that a hydrophilic peptide having a molecular weight above 100 D is of itself sufficient to stabilize sparingly water-soluble medicinal substances in dissolved form such that no further additions of organic solvents or solubilizing agents are necessary.

Such systems according to the invention can be in the form of liquid aqueous solutions, but the solvent can also be removed by suitable processes (for example spray drying or freeze drying). The products thus dried can be dissolved back to their initial state (redispersed) by addition of water or in the physiological medium.

According to the invention, the medicinal substance or medicinal substance mixtures are present in molecularly disperse form.

The extent to which and the limit concentrations, specific to the medicinal substance, at which the molecularly disperse content changes into a disperse system can be adjusted by selection of suitable hydrophilic peptides having a particularly high content of lipophilic regions and the like, and also by additives which can influence the helicality of the hydrophilic peptide, such as, for example, polyethylene glycols, surfactants and the like.

In this context, the medicinal substance in the form according to the invention can also be both partly molecularly disperse and partly disperse. Medicinal substances can thus also be present in colloidally disperse form (nanosols which are described in detail in numerous patent applications of ALFATEC-Pharma GmbH) up to coarsely disperse form.

By addition of softeners chosen from the group consisting of glycerol, propylene glycol, polyethylene glycols, triacetin, sorbitol, sorbitan mixtures, sorbitol solutions, glucose syrup, polyols and sugar-alcohols, and mixtures thereof, semi-solid to gel-like consistencies such as are known for conventional soft gelatin capsules or the cryopellets described in numerous patent applications of ALFATEC-Pharma GmbH can also be established.

A hydrophilic peptide in the context of the invention is understood as meaning a substance of naturally occurring, synthetic or partly synthetic origin which is built up from amino acids or derivatives of amino acids and has a molecular weight above 100 D.

It can be, in particular, collagen, collagen derivatives or substances derived from collagen from the following group: gelatin, fractionated gelatin, collagen hydrolyzate and gelatin derivatives; and mixtures thereof.

Hydrophilic peptides, such as, for example, plant proteins, plant protein hydrolyzates, elastin hydrolyzates, albumins, casein hydrolyzates and casein; and mixtures thereof are also included, according to the invention, in this definition.

It has furthermore been found that the use of a hydrophilic peptide as a solubilizing substance for sparingly water-soluble medicinal substances not only offers the advantage of stabilization of the medicinal substance in aqueous solution, but furthermore has more far-reaching benefits too.

The medicinal substance is present in a formulation according to the invention on the one hand protected from external influences, such as, for example, light, atmospheric oxygen and the like. If the formulation according to the invention is present in a solid, redissolvable form, protection of sensitive medicinal substances from moisture or access of moisture furthermore is ensured. Such medicinal substances in their formulations have therefore simultaneously proved to be active before losses in activity due to decomposition processes.

Hydrophilic peptides, in particular substances derived from collagen, have the additional advantage of being able to mask an unpleasant taste of the sparingly water-soluble medicinal substance in a formulation according to the invention. This masking of taste can be intensified further by addition of sorbitol, which, in addition to its property as a softener, advantageously has the function of a sweetener with a non-cariogenic property.

For the physiological background of absorption of medicinal substances in general and the improved absorption rate of the pellet formulations according to the invention to be explained adequately, it is first necessary to consider the mechanism of physiological absorption of medicinal substances as is also described in relevant publications. Nevertheless, the present invention neither is bound to the following attempt at a scientific explanation of the phenomena which occur according to the invention, nor can be limited thereby.

According to current knowledge (theory according to Brodie et al.), passive absorption of medicinal substances occurs when the following conditions exist:

a) the gastrointestinal membrane acts as a lipid barrier, b) the medicinal substance is taken in only in dissolved and non-charged, i.e. non-ionized, form, c) acid medicinal substances are absorbed preferentially in the stomach and basic medicinal substances preferentially in the intestine.

After peroral intake of a medicinal substance into the organism, its absorption, i.e. the transfer to the general circulation (biophase), is severely impeded by physical barriers, that is to say by the mucus layer and an aqueous layer adhering thereto the cell membranes of the intestinal epithelial cells with the glycocalyx covalently bonded thereto and the so-called "tight junctions" which join the epithelial cells to one another at their apical side.

These barriers mean that absorption of medicinal substances takes place chiefly according to their distribution mechanism and charge state—through the lipid double layers (so-called passive diffusion).

The epithelial cells of the entire gastrointestinal tract are covered with a mucus layer which comprises mucines (glycoproteins), electrolytes, proteins and nucleic acids. The glycoproteins in particular form a viscous gel structure with the main component of the mucus, that is to say water, and this structure primarily has protective functions for the underlying epithelial layer. The mucus layer is bonded to the apical surface of the epithelial cells via the glycocalyx. The glycocalyx also has a glycoprotein structure, which is bonded covalently to units of the membrane double layer of the epithelial cells. The branched polysaccharides of the glycocalyx, which are bonded covalently either directly to amphiphilic molecules of the double membrane or to the double membrane of incorporated proteins, have charged N-acetyl-neuraminic acid and sulfate radicals and are therefore negatively charged, which can lead to electrostatic bonding or repelling of charged molecules of medicinal substance or of electrostatically charged particles. The epithelial cell membranes comprise phospholipid double layers, into which proteins are anchored via their hydrophobic regions. The phospholipid double layers with their lipophilic content represent a further barrier to transportation of the medicinal substances to be absorbed.

The medicinal substance in a formulation according to the invention is evidently present both in molecularly disperse (dissolved) form and in conjugate bonding with the hydrophilic peptide, so that the known absorption barriers can be overcome better and absorption or bioavailability of a formulation according to the invention can be increased significantly.

Our own studies have shown that such an increase compared with conventional formulations can be achieved on administration in vivo.

Summarizing, it can thus be said that the present invention provides a pharmaceutical formulation of sparingly water-soluble medicinal substances in which the extent of in vivo absorption of the sparingly water-soluble medicinal substance from a molecularly disperse distribution in a hydrophilic peptide having a molecular weight above 100 D is increased compared with conventional formulations by 50% to 100%.

In addition to an increased absorption, an increased blood plasma concentration and a faster increase therein compared with commercially available preparations is also to be found.

The increased absorption rate of the medicinal substance from a formulation according to the invention furthermore can be demonstrated very impressively if, for example, the peroral administration route of a pharmaceutical formulation is considered:

After a formulation according to the invention has been redissolved in the physiological medium, the molecularly disperse distribution of a sparingly water-soluble medicinal substance is astonishingly retained. The release of the medicinal substance from its formulation occurs without a prior equilibrium process, in contrast to conventional formulations comprising solubilizers. Precipitation or flocculation from gelatin or a substance derived from collagen due to the inter- and intramolecular conjugates or inclusions formed with the substances to be absorbed, furthermore, are effectively prevented. This enclosing (viscous) sol layer protects the medicinal substance, for example, from physiological influences, so that it is not displaced from the conjugate with the gelatin. Retention of the molecularly disperse distribution of the medicinal substance from release from the drug form to subsequent absorption is advantageously ensured in this manner. This protection can be intensified further by incorporating customary pharmaceutical auxiliaries, such as, for example, buffer substances (for example disodium hydrogen phosphate) into the formulation.

A composition according to the invention of a sparingly water-soluble medicinal substance and gelatin which melts in the physiological medium furthermore shows a high affinity for mucous membrane surfaces. This adhesion or sticking to the mucous membrane (bioadhesion) causes direct contact between the medicinal substance and the physiological absorption barrier.

Surprisingly, medicinal substances which have bioavailability problems in conventional crystalline form because of their poor wettability are redissolved from a solid or dry formulation according to the invention in the physiological medium without such problems and are available for absorption in molecularly disperse form. For this reason, the use of relatively large amounts of surfactants or wetting agents, such as is necessary and customary for conventional formulations in order to render sparingly water-soluble medicinal substances adequately wettable at all, can be dispensed with.

Astonishingly, no further changes at all to crystal modifications of a medicinal substance take place because of the molecularly disperse distribution of the medicinal substance in the formulations according to the invention. The invention can thus advantageously also be employed for those medicinal substances which tend towards changes in modification during preparation or storage of a corresponding drug form and therefore result in bioavailability problems.

The dissolving operation from a formulation according to the invention, as the time-determining factor, depends exclusively on the nature and composition of the hydrophilic peptide chosen, and can be modulated in release. Acute forms as well as sustained release forms can thus be formulated.

Gelatin is a scleroprotein which is obtained from collagen-containing material and has different properties, depending on the preparation process. It essentially comprises four molecular weight fractions, which influence the physico-chemical properties as a function of the molecular weight and percentage weight content. For example, the higher the microgel ($10^7$ to $10^8$ D) content, the higher also the viscosity of the aqueous solution. Commercially available grades comprise up to 15% by weight of microgel. The fractions of alpha-gelatin and oligomers thereof ($9.5 \times 10^4 / 10^5$ to $10^6$ D) are decisive for the gel firmness and are usually between 10 and 40% by weight. Molecular weights below alpha-gelatin are called peptides and can make up to 80% by weight of conventional gelatin grades (low-Bloom).

Gelatin has temperature- and concentration-dependent sol-gel conversion properties which depend on the molecular composition. The Bloom rating is stated as the conventional method of determining the gel formation capacity. Low commercial grades start at 50 Bloom, high-Bloom grades are about 300 Bloom.

The chemical and physical properties vary according to the preparation process, gelatin grades obtained under particularly gentle conditions (low content of dextrorotatory amino acids and peptides) having short sol-gel conversion rates and melting points above 37° C. (measured as a 10% strength solution). The secondary and tertiary structure of collagen in the gelatin is largely retained with a particularly gentle preparation procedure.

Fractionated gelatin is the specific case of gelatin and is obtained from conventional gelatin by special preparation techniques, such as, for example, ultrafiltration. The composition can be varied, for example, by removal of peptides (molecular weight<$9.5 \times 10^4$ D) or by mixtures of individual fractions, such as, for example, alpha-chains, dimeric and trimeric chains or microgel.

Gelatin or fractionated gelatin furthermore has good surfactant properties with a protective colloid action and emulsifier properties.

Collagen in its natural form is water-insoluble. Due to special preparation processes, there are now soluble types of collagen having an average molecular weight of about 300,000 D.

Collagen derivatives are modified collagen molecules which can be crosslinked three-dimensionally, for example, with crosslinkers or can be chemically crosslinked, for example, in a different manner.

Gelatin derivatives are chemically modified gelatins, such as, for example, succinylated gelatin, crosslinked polypeptides or oxypolygelatin, which are also known as plasma expanders. Such plasma expanders can also comprise special electrolyte additions.

Collagen hydrolyzate is understood as a product which is obtained from collagen or gelatin by hydrolysis under pressure or enzymatically and no longer has a sol-gel transition capacity.

Collagen hydrolyzates are readily soluble in cold water and the molecular weight composition can be between a few hundred D to below $9.5 \times 10^4$ D. Products obtained by an enzymatic route are more homogeneous in molecular composition and also have a good surfactant and emulsifier action.

The plant proteins and hydrolyzates thereof are newly developed products which largely correspond to collagen hydrolyzates in their properties. They are preferably obtained from wheat and soya and have, for example, molecular weights of 200,000–300,000 D or 1,000–10,000 D respectively.

Elastin hydrolyzates are obtained enzymatically from elastin and consist of a single polypeptide chain with a high content of non-polar amino acids. They can therefore also be used in lipophilic systems. Elastin hydrolyzates have a molecular weight of 2,000–3,000 D and are highly film-forming on the skin.

The medicinal substance can be stabilized in a molecularly disperse form in the helical regions of the hydrophilic peptide, for example, by lipophilic interactions, hydrogen bridges, ionic interactions, polar interactions, dipole-dipole interactions and the like.

The helicality depends on the molecular composition, the polymolecularity, the degree of racemization of the alpha C atoms in the peptide units, the content of proline and hydroxyproline and the content of helicophobic amino acids. These parameters can be influenced within wide limits by suitable preparation processes.

When a formulation according to the invention is redissolved, these helical structures are reconstituted very rapidly, above all in the physiological medium at 37° C. This takes place even if the concentrations of hydrophilic peptide present are very low.

Due to such an order principle in the molecular range, the medicinal substance remains added on to the helix in the molecularly disperse form (conjugate formation) and is thus protected effectively from precipitation or flocculation. A medicinal substance can therefore ideally be absorbed directly from such a stabilized system according to the invention.

In the case of medicinal substances which are extremely unstable to heat, another embodiment of the invention advantageously allows provision of formulations having properties according to the invention which are prepared under exclusively cold conditions, i.e. at room temperature without using heat, for example by lyophilization. A hydrophilic peptide chosen from the group consisting of: plant proteins, plant protein hydrolyzates, elastin hydrolyzates, collagen hydrolyzates, gelatin which is soluble in cold water and gelatin derivatives; and mixtures thereof; with a maximum of the molecular weight distribution below $10^5$ D, can be used in this procedure.

This embodiment of the invention furthermore provides a formulation which dissolves in cold water particularly rapidly, as a rule within 2 minutes. Such a formulation is suitable for pharmaceutical acute forms and products for parenteral administration, as well as for the preparation of drinking solutions or instant formulations for internal and external use.

Hydrophilic peptides which have sol-gel-forming properties, such as, for example, gelatin or fractionated gelatin, can also be used according to the invention. Depending on their molecular composition, such substances can be used, for example, for solid formulations which release the medicinal substance rapidly or slowly in an aqueous medium at 37° C.

Slow-releasing formulations can also be used for the preparation of a sustained release form which releases the medicinal substance linearly.

In addition to the hydrophilic peptides, the customary auxiliaries can be used for retardation for such sustained release formulations, for example alginates, cellulose derivatives, polyvinylpyrrolidone, naturally occurring or modified starches, polyacrylic acid and polymers of methacrylic acid and methacrylic acid esters, hydrophilic gums and the like; and mixtures thereof.

Pharmaceutically acceptable crosslinking agents, such as, for example, citral, xylose or other aldoses, and the like, can also advantageously be used for preparation of formulations according to the invention.

In addition to their use for retardation purposes, these substances can also have other effects when added in a small amount, in particular to gelatin. For example, they have the property of linking the triple helices of gelatin to one another. If this happens at only a few points, the properties of the gelatin macromolecule are retained in a form such that the medicinal substance is effectively stabilized and fixed in the molecular associations in molecularly disperse form.

Helical structures of the hydrophilic peptide, for example of gelatin or fractionated gelatin, furthermore, can be influenced greatly by additives such as, for example, softeners, surfactants and the like. Thus, for example, glycerol, polyethylene glycols and the like promote the formation of helical conformations and also contribute advantageously to the stabilization of a molecularly disperse system according to the invention.

Surprisingly, it has additionally been found that a combination of gelatin with softeners acts as a so-called "enhancer" (absorption accelerator). The absorption process of a medicinal substance is thereby facilitated or accelerated considerably, and above all increased significantly compared with the formulations of the prior art.

The present invention therefore also provides an enhancer, which comprises a combination of at least one hydrophilic peptide chosen from the group consisting of: collagen, collagen derivatives, gelatin, fractionated gelatin, collagen hydrolyzates, gelatin derivatives, plant proteins, plant protein hydrolyzates, elastin hydrolyzates, albumins and casein hydrolyzates; caseins; and mixtures thereof; with a softener which is chosen from the group consisting of: glycerol, propylene glycol, polyethylene glycols, triacetin, sorbitol, sorbitan mixtures, sorbitol solutions, glucose syrup, polyols and sugar-alcohols; and mixtures thereof.

Another embodiment of the present invention is thus to be found, in particular, in sparingly water-soluble peptide medicinal substances, such as, for example, renin antagonists. Since peptide medicinal substances are subject to increased enzymatic breakdown (inactivation even before absorption) by physiological enzymes in the gastrointestinal tract after administration, attempts are made to stabilize the peptide medicinal substance against the gastrointestinal enzymes by derivatization, for example by introduction of protective groups. However, the lipophilic character of such medicinal substance molecules thereby increases, which is associated with a deterioration in their water-solubility.

Such derivatized peptide medicinal substances may be particularly suitable for preparation of a molecularly disperse distribution according to the invention. Interactions of lipophilic molecular portions with lipophilic regions in the helical structures of the hydrophilic peptide can advantageously be utilized here for stabilization of the molecularly disperse system.

Such formulations according to the invention which comprise peptide medicinal substances can advantageously simultaneously comprise customary penetration accelerators (enhancers) or protease inhibitors.

Conventional penetration accelerators can be divided, for example, into the following groups:

chelating agents, such as, for example, ethylenediaminetetraacetic acid (EDTA), citric acid, salicylates, N-acyl derivatives of collagen or substances derived from collagen and N-amino-acyl derivatives of beta-diketones (enamines);

surfactants, such as, for example: sodium lauryl sulfate, polyoxyethylene-9 lauryl ether and polyoxyethylene-20 cetyl ether;

non-surfactants, such as, for example, unsaturated cyclic urea compounds and 1-alkyl- and 1-alkenylazacycloalkanone derivatives;

bile acid salts and derivatives, such as, for example, sodium deoxycholate, sodium glycocholate, sodium taurodihydrofusidate (STDHF) and sodium glycodihydrofusidate;

fatty acids and derivatives, such as, for example, oleic acid, caprylic acid, capric acid, acylcarnitines and acylcholines and their mono- and diglycerides.

In this manner, especially in the case of peptide medicinal substances, their known low absorption rate in the gastrointestinal tract can be increased still further than is in any case already possible with a formulation according to the invention without additional penetration accelerators.

The hydrophilic peptide, such as, for example, gelatin, also has another property here. Mucous membrane-irritating actions of customary penetration accelerators can be effectively reduced.

If the formulations according to the invention comprise softeners, these can have a semi-solid to gel-like consistency and can be used either in the form of cryopellets, for example as a single-dosed drug form, or for capsule fillings, for example in soft gelatine capsules.

Conventional capsule filling recipes in many cases comprise solutions of sparingly water-soluble medicinal substances in organic solvents, solvent mixtures of complicated composition and solubilizing agents, such as, for example, polyethylene glycols, 1,2-propylene glycol, 1,3-butanediol, 1,4-butanediol, 1,2-propanediol, polyoxyethylene/polyoxypropylene copolymers, tetrahydrofurfuryl alcohol and other polyhydric alcohols.

If systems according to the invention are thus employed as fillings for conventional soft gelatin capsules, the following advantages result:

The amount of conventional solvent mixtures of complicated composition (see above) can be reduced or individual components can be dispensed with entirely.

No flocculation or precipitation of sparingly water-soluble medicinal substances takes place, such as may occur with conventional filling recipes in the physiological medium.

Known pharmaceutical substances which are used as solubilizing agents can be reduced in their amount by the present invention or, in combination with the hydrophilic peptide according to the invention, can lead to new properties of the pharmaceutical formulation. Thus, in particular, even substances such as, for example, polyethylene glycol 200 or 400, tetrahydrofurfuryl alcohol polyethylene glycol ether or 1,2-propyleneglycol can lead to these new properties.

Medicinal substances which cannot be dissolved or can be dissolved in only a small amount can likewise also be converted into a form having new properties, it being possible for the medicinal substance to be present in part in the form dissolved (molecularly disperse) according to the invention and, at the same time, in a disperse or coarsely disperse form. The same also applies to emulsions.

Surfactants undergo severe interactions, for example complexes, with hydrophilic peptides, such as, for example, gelatin or collagen hydrolyzates. This complexing is greater the more polar, for example, a surfactant anion (for example sodium lauryl sulfate, sodium dioctyl sulfosuccinate). This means that the solubilizing property according to the invention of the hydrophilic peptides can be expediently combined with that of surfactants.

Hydrotropic substances, such as, for example, urea, N-methylacetamide or nicotinic acid, can be used according to the invention in the same sense as surfactants.

The presence of gelatin or of a substance derived from collagen, as a macromolecule of primarily biogenic origin, furthermore ensures the greatest possible tolerability of a drug formulation according to the invention in the organism. Undesirable side effects of auxiliaries, for example irritation of mucous membranes, such as may be caused, for example, by organic solvents or surfactants, are thus eliminated entirely or can at least be reduced decisively.

As is known, gelatin has an isoelectric point in the acid range (gelatin type B) or in the alkaline range (gelatin type A), depending on its preparation process. This property can be utilized according to the invention for direct formation of micro- or nanocapsules in a molecularly disperse distribution of the medicinal substance and, for example, substances derived from collagen. Thus, if gelatins of opposite charge are used as a mixture with a solution containing the medicinal substance (for example at a pH of 6–7), microcapsules can be prepared by removing the solvent. If gelatin grades or collagen derivatives of defined molecular composition are used, three-dimensional crosslinkings can be carried out in the nanometer range. Gelatin or collagen hydrolyzates furthermore can form conjugates with a medicinal substance, for example with an approximately 2–3% addition of salts.

The present invention thus represents an extremely valuable contribution to appropriate therapeutic utilization and use of drugs according to the invention comprising sparingly water-soluble medicinal substances.

The terms "active compounds" and "medicinal substances" are used synonymously in the context of the present invention and, by definition, include both substances which can be biologically active and are not or not yet employed therapeutically, and medicinal substances which are supplied to the organism and interact with it.

Sparingly water-soluble medicinal substances in the context of the present invention are understood as meaning medicinal substances which have substance properties such as low solubility, poor wettability and metastable modifications and thereby lead to bioavailability problems.

The term "sparingly water-soluble" in the context of the present invention is understood as comprising the terms described in the pharmacopeias for solubilities such as "of low solubility", "slightly soluble", "very slightly soluble" to "practically insoluble".

The term "medicinal substance" is defined according to the invention as follows:

Medicinal substances may be synthetic, partly synthetic or natural in origin, both chemically uniform substances or substance mixtures, and also combinations of various pharmacologically active components. The term medicinal substance furthermore, however, is also to include plant drugs and plant extracts generally, and, finally, also to incorporate hormones, vitamins and enzymes.

Enantiomerically pure active compounds or pseudoracemates are also suitable according to the invention. Active compounds from the field of dietary foodstuffs (health care) and from the field of cosmetics furthermore can be used.

There is no limitation at all in respect of chemical substance classes in the case of sparingly water-soluble medicinal substances which are suitable for the invention. Chemical substance classes and some associated representatives are mentioned by way of example below:

1. Phenylethylamine derivatives, such as, for example, salbutamol and chloramphenicol;
2. Phenyl-propylamine derivatives, such as, for example, haloperidol;
3. Phenylbutylamine derivatives, such as, for example, fluspirilene and verapamil;
4. Arylalkanoic acid derivatives, such as, for example, diclofenac and indometacin;
5. Diphenylmethane derivatives, such as, for example, chlorphenoxamine and diphenhydramine;
6. Dibenzocycloheptadienes and dibenzocycloheptatrienes, such as, for example, amitriptyline;
7. Steroid derivatives, such as, for example, fluocortolone and cortisone acetate;
8. Phenol ethers, such as, for example, bezafibrate and etacrynic acid;
9. 4-Aminobenzoic acid derivatives, such as, for example, bromhexine;
10. Anilide derivatives, such as, for example, paracetamol;
11. Aniline derivatives, such as, for example, mefenamic acid;
12. Aromatic carboxylic acids and derivatives, such as, for example, acetylsalicylic acid;
13. Aryloxypropylamine derivatives, such as, for example, propranolol;
14. Sulfonamide derivatives, such as, for example, sulfaguanidine, furosemide and sulfamethoxazole;
15. Sulfonylurea derivatives, such as, for example, glibenclamide;
16. Beta-lactam antibiotics having a benzylpenicillin, phenoxymethylpenicillin or cefalosporin C-base structure, such as, for example, penicillin V and amoxicillin;
17. Furan derivatives, such as, for example, nitrofurantoin;
18. Tetrahydrofuran derivatives, such as, for example, mefruside;
19. Pyrazole derivatives, such as pyrazolinone derivatives or pyrazolidine-3,5-diones, such as, for example, oxyphenbutazone;
20. Imidazole derivatives, such as, for example, clotrimazole, cimetidine and benzimidazoles, such as, for example, omeprazole;
21. Imidazolidine derivatives, such as, for example, phenytoin;

22. 1,3,4-Thiadiazole derivatives, such as, for example, acetazolamide;
23. Pyridines, such as, for example, niflumic acid;
24. Piperidine derivatives, such as, for example, pethidine;
25. Isoquinoline derivatives, such as, for example, papaverine;
26. Thioxanthene derivatives, such as, for example, chlorprothixene;
27. Pyrimidine derivatives, such as, for example, brivudine, hexahydropyrimidines, uracils, barbituric acid derivatives, such as, for example, allopurinol, secbutabarbital, and furthermore pyrazine, piperazine and quinazoline derivatives;
28. Phenothiazine derivatives and azaphenothiazine derivatives, such as, for example, chlorpromazine;
29. 1,2,4-Benzothiadiazines, such as, for example, hydrochlorothiazide;
30. Dibenzoazepine derivatives, such as, for example, imipramine;
31. Benzodiazepine derivatives, such as, for example, diazepam, oxazepam and chlordiazepoxide;
32. Purines, such as, for example, theophylline;
33. Pteridines, such as, for example, methotrexate and triamterene;
34. Nitric acid ester derivatives, such as, for example, isosorbide dinitrate;
35. Peptide medicinal substances, such as, for example, renin antagonists;

furthermore medicinal substances from the groups consisting of derivatives of aliphatic carboxylic acids, naphthalene derivatives, anthracene derivatives, pyrrole derivatives, pyrrolidine derivatives, both pyrrolidinone and pyrrolidinedione derivatives, thiophene derivatives, isoxazole derivatives, oxazole and oxazolidine derivatives, 2-imidazoline derivatives, benzimidazole derivatives, 1,3-thiazole, 1,3-thiazolidine and 1,2,5-thiadiazole derivatives, chroman derivatives, quinoline derivatives, morpholines, morphine-like compounds, amino alcohols, guanidine and biguanide derivatives, oxazaphosphorines, adamantane derivatives, substances of natural, partly synthetic or synthetic origin built up from isoprene units, and the like.

They can also be generally organic or inorganic as well as organometallic substances for which solubilization seems appropriate.

The formulations according to the invention can thus also advantageously be employed, for example, in the preparation of photographic layers.

The process for the preparation of a formulation according to the invention comprising sparingly water-soluble medicinal substances is described below.

Other embodiments in this context are described in the patent applications of ALFATEC Pharma GmbH, where appropriate GGU mbH & Co. KG of the same day entitled "Solid and liquid solutions of Flavonoids" (11AL2725), "Pharmaceutical formulation having the action of Gingko biloba extract" (11AL2728) and "Solid and liquid solutions of Gingko biloba extract" (11AL2726), the content of which is also made the subject-matter of the disclosure of the present patent application.

In the simplest case, the process according to the invention for the preparation of a formulation comprising sparingly water-soluble medicinal substances can be described by the following process steps:

a) The medicinal substance is suspended or dissolved in a solvent and this suspension or solution is mixed with an aqueous solution of a hydrophilic peptide having a molecular weight above 100 D.

b) The solvent or solvents are removed from this solution.

The ratio of the amount of medicinal substance to the hydrophilic peptide is usually 1:0.5 to 1:1000, but in particular 1:2 to 1:50, stated in parts by weight of dry substance.

Other additional hydrophilic macromolecules which intensify, and under certain circumstances may even potentiate, the solubilizing action of the hydrophilic peptide, such as, for example, agar-agar, gum arabic, pectins, tragacanth, xanthan, naturally occurring and modified starches, dextrans, dextrins, maltodextrin, chitosan, alginates, cellulose derivatives, polyvinyl alcohol, polyvinylpyrrolidone, polyethylene glycols, polyacrylic acid and polymers of methacrylic acid and methacrylic esters; and mixtures thereof, can be added to this system according to the invention.

The weight ratio of these hydrophilic macromolecules to the hydrophilic peptide can be up to 1:1.

If appropriate, other carriers and auxiliaries which are suitable for the corresponding use can be added to the system prepared by the described process according to the invention. Such substances can be, for example, customary pharmaceutical carriers and auxiliaries from the following groups:

1. Additional matrix-forming agents, for example dextrans, saccharose, glycine, lactose, sorbitol, polyvinylpyrrolidone and mannitol; and mixtures thereof.
2. Fillers, for example starch.
3. Surfactants, for example polysorbates.
4. pH correctants and buffer substances, for example disodium citrate, disodium phosphate and the like.
5. Dyestuffs, for example curcumin.
6. Aromatizing additives or flavor correctants, for example fruit extracts, fruit juice concentrates and the like.

In one embodiment of the process step described under a), the sparingly water-soluble medicinal substance can be dissolved or suspended in water-miscible organic solvents. Water may already be present, but is not absolutely necessary.

Organic solvents which can be chosen for the sparingly water-soluble medicinal substance are, for example, water-miscible organic solvents from the group consisting of: water-miscible organic solvent systems; lower alcohols, such as, for example, methanol, ethanol and isopropanol; lower ketones, such as, for example, acetone; glycerol, polyethylene glycols, 1,2-propylene glycol and tetrahydrofurfuryl alcohol polyethylene glycol ether (tetraglycol); lower ethers; lower esters; and mixtures thereof.

Depending on the lipophilic or hydrophilic character of the medicinal substance, a clear solution or a suspension of the sparingly water-soluble medicinal substance may result before mixing with the hydrophilic peptide, which is advantageously present in aqueous solution.

The stable solutions of the sparingly water-soluble medicinal substance which are obtained by this simple process can already be regarded as medicinal formulations and can also be used as such.

However, the stability of the aqueous/organic system under in vitro and also in vivo conditions is not bound to the presence of the organic solvent, such as, for example, alcohol, which could initially be assumed. This fact can easily be demonstrated by removal of the alcohol, for example by evaporation, in contrast to commercially available drug formulations (liquid drug formulations for oral or peroral intake, such as, for example, drops) of the prior art.

The organic addition in the products according to the invention could probably thus have a vehicle function, for example in that by changing the hydrate shell of the substance derived from collagen, such as gelatin, the lipophilic areas thereof are activated. Interactions between the gelatin and lipophilic molecular portions of a sparingly water-soluble medicinal substance molecule can preferentially take place in this manner.

Modification of the process step described under a) results in the case of hydrophilic peptides which dissolve in cold water (water at room temperature), such as, for example, collagen hydrolyzates or gelatin derivatives. For example, these substances can be mixed directly with an aqueous/alcoholic solution of a sparingly water-soluble medicinal substance and thus dissolved therein.

Another embodiment of the process step described under a) for the preparation of liquid, aqueous and stable solutions of a medicinal substance in the context of the invention can be used if this is soluble in an acid or basic medium, for example to form a salt. Organic solvents can be dispensed with in part, but surprisingly also entirely, in this process variant.

The procedure according to the invention is described here by way of example for a medicinal substance which can be converted into solution in a basic medium with salt formation:

Such a medicinal substance is preferably dissolved in an aqueous-ammoniacal medium at pH values above 7 and mixed homogeneously with the hydrophilic peptide, or aqueous solutions thereof, such that a clear solution is formed. If the medicinal substance can be decomposed, for example by access of carbon dioxide, the procedure is advantageously carried out under an inert gas atmosphere (for example gassing with nitrogen or argon).

The salt formation can then be reversed by addition of acid, or the ammonia can preferably be removed by the methods mentioned in the process step of drying (b) described below, for example by simple evaporation or freeze drying.

The procedure is the reverse for medicinal substances having a basic character.

However, not every medicinal substance can be dissolved in an aqueous medium to form a salt, since salts of medicinal substances may also be sparingly water-soluble. Nevertheless, in a further embodiment of process step a) according to the invention, solutions of such substances can be prepared with salt formation in the abovementioned organic solvents, in particular polyethylene glycols, 1,2-propylene glycol or tetrahydrofurfuryl alcohol polyethylene glycol ether (tetraglycol). It is thus known, for example, of glibenclamid or indomethacin, that these substances can be dissolved in polyethylene glycols by means of addition of ammonia.

If these (anhydrous) solutions of medicinal substance salts are added to an aqueous solution of the hydrophilic peptide, which has first been brought to a pH which reverses the salt formation, or if the aqueous solution of the hydrophilic peptide is brought to a pH which reverses the salt formation only after addition of the organic salt solution, medicinal substance solutions according to the invention are likewise obtained.

In this case, the organic solvent used does not have to be removed from the formulation, since it simultaneously has a softener function, for example in the case of cryopellet preparation according to the invention using gelatin or other substances derived from collagen.

In another embodiment of stage a) of the process according to the invention, a sparingly water-soluble medicinal substance is first mixed with the hydrophilic peptide in the dry state and, after addition of one of the volatile organic solvents described (for example alcohol), is kneaded with this. After the solvent has dried, a pulverizable composition having the properties described according to the invention is obtained.

In another embodiment of the process according to the invention, after conversion into solution, the medicinal substance can be applied directly to the hydrophilic peptide, for example by spraying on in a fluidized bed unit.

In process step a), dehydrating agents, such as, for example, the organic solvents listed, can be used in all the embodiments described for the process according to the invention. After loosening of the triple helical structure, for example of gelatin or fractionated gelatin, such additives can cause a trans-cis change in conformation of the now free alpha chains, so that the medicinal substance can preferentially interact with the lipophilic regions of the gelatin or fractionated gelatin (conjugate formation). After rehydration, the medicinal substance in question is incorporated into the original gelatin conformation which has reformed very rapidly.

In the process step specified under b), the solvent or solvents from the mixture obtained in stage a) of the process according to the invention are removed. This can be effected, for example, by concentration, evaporation, drying or combinations of the processes mentioned, it being possible for various process variants to result.

Variant A

In one embodiment of process step b) according to the invention, for example, gelatin granules having properties according to the invention can be obtained by simple drying in air and subsequent grinding. The drying can be carried out in vacuo (about 3000 to 5000 Pa (about 30 to 50 mbar)), for example at drying temperatures of up to 50° C., in order to accelerate the drying operation and to maintain low temperatures.

Variant B

Water or a volatile organic solvent or the ammonia are removed by customary spray drying. A usually dry powder is obtained. Air with an intake temperature of between 100° C. and 300° C. is usually used as the process gas in conventional spray drying units, in which case an average temperature difference between the process gas and goods of 50° C. to 100° C. may result. If substances which are particularly sensitive to oxidation are present, an inert gas, such as, for example, nitrogen, can also be employed as the process gas.

Organic solvents can be removed before the spray drying, for example by evaporation, and can in this way be recovered easily and economically for renewed use.

Variant C

The formulation is converted into the dry, solid state by customary freeze drying.

Freezing of the formulation can be carried out, for example, in the freeze drying unit itself, for example in a range from −10° C. to −40° C. Complete freezing can easily be detected by a sudden change in the conductivity in the sample to be frozen. The actual drying is carried out at temperatures 15° C. below the sublimation point of water under a pressure of 0.1 Pa to $10^2$ Pa (0.001 mbar to 1.03 mbar). The drying operation, which can proceed in a conventional freeze drying unit (condenser temperature: about −40° C.) at −25° C. and 33 Pa (0.33 mbar) in primary drying with sublimation of the frozen water leads to a freeze-dried product after secondary drying (desorption).

Organic solvents can be removed before the spray drying, for example by evaporation, and can in this way be recovered easily and economically for renewed use.

In another embodiment of the process according to the invention, liquid formulations according to the invention of sparingly water-soluble medicinal substances can be further processed to solid or semi-solid or gel-like shaped articles. Such formulations are distinguished by a stable fixing of the molecularly disperse state of the sparingly water-soluble medicinal substance in a matrix of the hydrophilic peptide, in particular substances derived from collagen. They can be converted back completely into a stable, liquid, dissolved state (redispersed) in an aqueous or physiological medium.

Such formulations can preferably be shaped directly, or after concentration, by means of the Cryopel$^R$ process (Messer Griesheim GmbH) in liquid nitrogen to give the cryopellets described in numerous patent applications (for example patent application P 42 01 179.5 of 17.01.1992) of ALFATEC-Pharma GmbH and then freeze dried. Freeze-dried cryopellets are obtained in this manner by a gentle process which is suitable for sensitive medicinal substances, while retaining the properties according to the invention, and, for example, because of their storage stability, high mechanical stability, good flow properties and diameter which can be varied from 0.2 to 12 mm, inter alia, can be either introduced into conventional hard gelatin capsules or, when introduced into metered dispensers, can be used as single-dosed acute forms.

Formulations which can be dissolved extremely rapidly in cold water ("solid drops") can be prepared by means of freeze drying by suitable auxiliary additives, such as, for example, mannitol.

If the hydrophilic peptide has sol/gel-forming properties, such as, for example, if gelatin or fractionated gelatin having a maximum of the molecular weight distribution of above about $9.5 \times 10^4$ D is used, semi-solid to gel-like consistencies of the formulation such as are also known from conventional soft gelatin capsules can be established by addition of the softeners described.

The ratio of the amounts of hydrophilic peptide to softener can be varied from 1:0.001 to 1:50, in particular from 1:0.1 to 1:5, stated in parts by weight.

It is found that the softener substances, which from the chemical point of view belong to the group of polyols, as well as having an influence on the hydrated shell of the hydrophilic peptide, such as, for example, gelatin or fractionated gelatin, associated with activation of lipophilic molecular regions, can also determine the stabilization and the degree of helical conformation of these molecules. Even more intensive interactions (conjugate formation) can thereby take place between the gelatin or fractionated gelatin and lipophilic molecular portions of a medicinal substance according to the invention. Astonishingly, a very high degree of charging of the matrix according to the invention with the medicinal substance can thus be chosen (up to 0.5:1), without problems resulting with the stability of the molecularly disperse distribution.

Such a formulation according to the invention can be shaped in a particularly gentle manner and to an optically attractive product having astonishing technological diversity and advantages to give cryopellets, which can be prepared by direct dropwise addition or metering of the composition to be processed into an immersion bath with liquid nitrogen, for example by means of the Cryopel$^R$ process (see above). If required, a product which can advantageously be introduced into hard gelatin capsules, is optically very attractive and is obtained by a simple and economic route, the properties according to the invention being retained, can be obtained by drying such cryopellets.

Such semi-solid to gel-like formulations can also serve either as the filling for conventional soft gelatin capsules or as the filling for soft gelatin capsules which are shaped by metering into liquid nitrogen. Semisolid compositions can also be metered into other suitable containers, such as, for example, cooled blisters or similar hollow forms. The blisters can then be sealed directly, and single-dosed drug forms are obtained.

In addition to the embodiments of the process according to the invention which have already been mentioned so far, another embodiment results from the knowledge of the quality of the hydrophilic peptide employed.

As regards substances derived from collagen, for example, it is known that their ash content, i.e. the degree of desalination, varies as a function of the preparation. The ash content of commercially available gelatin grades can be up to 2% by weight. However, the residual ash content of good qualities resulting from the preparation lies at values below 0.2% by weight.

On the other hand, it is known of sparingly water-soluble medicinal substances, for example of medicinal substances having a polar character, that they can form complexes with calcium ions or magnesium ions. These additions of divalent ions cause a conjugate (complexing) of the two components by interaction with the polar groups of these substances.

Interactions of such complexes of sparingly water-soluble medicinal substances with calcium salts or magnesium salts with the functional groups of a hydrophilic peptide lead to effective stabilization of the molecularly disperse state in the context of the invention, which would not be possible without the hydrophilic peptide and therefore would lead to precipitation of the sparingly water-soluble medicinal substance in the physiological medium.

In this embodiment of the process according to the invention, for example, a commercially available gelatin having a relatively high ash content (salt content) is thus therefore used. On the other hand, a defined amount of calcium salts or magnesium salts (for example 1 to 2% by weight of calcium chloride or magnesium chloride) can be added in a controlled manner to a gelatin grade which is completely desalinated as a result of the preparation.

The calcium ions furthermore promote absorption of the sparingly water-soluble medicinal substance by complexing with constituents of the cell membrane.

The formulations according to the invention of a sparingly water-soluble medicinal substance can be suitable both for pharmaceutical and cosmetic or for dietary (health care) purposes.

Pharmaceutical formulation in the context of the invention is understood as meaning both medicament formulations and cosmetic or dietary foodstuffs formulations (health care).

By make-up in suitable containers (for example sachets), pulverulent formulations can be used for preparation of liquid aqueous drug solutions for intake. The powder can likewise be introduced into customary hard gelatin capsules or further processed to conventional pellets or granules and then introduced into hard gelatin capsules. Compression by customary methods to give tablets, preparation of coated tablets, preparation of enteric-coated drug forms and the like, if appropriate using customary tableting auxiliaries, such as, for example, FST complex, is also possible. Formulations according to the invention which comprise substances derived from collagen, such as, for example, collagen hydrolyzates, are advantageously suitable for direct tableting.

Formulations which have been lyophilized according to the invention, especially using low molecular weight gelatin grades, collagen hydrolyzates or gelatin derivatives, can be redissolved in an accelerated manner in cold water. Such formulations can also serve as a basis for sterile drug forms, such as, for example, products for parenteral administration or ophthalmic agents. Customary two-chamber syringes, for example, can be used here as containers for injection solutions.

Parenteral drug forms in the context of the invention are distinguished in particular by a high tolerability because of the simple composition of the system, using acceptable auxiliaries which have been proven for intravenous purposes.

Transdermal formulations and processing of a formulation according to the invention with customary auxiliaries to give a transdermal formulation are also possible.

Drug formulations according to the invention can also be employed for nasal or pulmonary administration. Pulverulent systems can be used, for example, for the preparation of inhalation drug forms. Cryopellets can preferably be suitable for nasal administration purposes, for example because of pronounced bioadhesive properties.

Beyond this, the systems according to the invention can also be used as dietary foodstuffs (health care) or be used in industrial sectors, depending on the substances to be solubilized which are employed.

By the present invention, it is likewise possible also to bring sparingly water-soluble, synthetic or plant sweeteners into a solubilized form, for example for use as dietary foodstuffs. For example, it is known of stevioside, a diterpenic acid glucosyl-sophoroside from Stevia rebaudiana, that although the sweetening action is 150 to 300 times more potent than that of sucrose, the substance itself dissolves poorly in hot drinks. Stevioside which is present in cryopelleted form and is solubilized according to the invention can be made up particularly advantageously into dosed dispensers for individual removal.

The expert can easily develop further process variants independently in the context of his expert knowledge. The following examples are intended to illustrate the invention in more detail:

EXAMPLE 1

1,400 g of gelatin powder (30 Bloom) are preswollen in 14 l of distilled water for 20 minutes and a solution is then prepared at 40° C.

100 g of hydrochlorothiazide are dissolved in 7 l of ethanol and the solution is mixed homogeneously with the gelatin solution until a clear solution is formed.

After evaporation of the ethanol, the solvent is removed by spray drying, during which the intake temperature of the process gas is up to 180° C. and the outlet temperature is 80° C., to give a powder.

150 mg of the powder (corresponding to 10 mg of hydrochlorothiazide) are redissolved in 25 ml of simulated gastric juice at 37° C. A clear solution results.

After dry granulation, the resulting powder is mixed with customary tableting auxiliaries (FST complex) and pressed on a tableting machine to tablets having a content of 10 mg of hydrochlorothiazide.

EXAMPLE 2

The example is carried out analogously to Example 1 using a gelatin powder of 150 Bloom.

The powder obtained analogously to Example 1 is mixed with lactose as a filler and further processed to hard gelatin capsules having a content of 10 mg of hydrochlorothiazide.

EXAMPLE 3

150 g of commercially available collagen hydrolyzate 150 g of mannitol 700 g of distilled water The mannitol and the collagen hydrolyzate are dissolved in 350 g of the water. A pH of between 8 and 10 is established by addition of ammonia solution.

50 g of quercetin are dispersed homogeneously in 350 g of water and a pH of between 8 and 10 is established by means of ammonia solution, while gassing with nitrogen.

The two solutions are mixed and pellets having a diameter of 5 mm are formed by dropwise addition of the composition into an immersion bath with liquid nitrogen by means of the Cryopel$^R$ metering system.

The frozen pellets are dried in a freeze drying unit with a primary drying at −25° C. under 5 Pa (0.05 mbar) and a secondary drying at 22° C.

The dried pellets can be introduced into a metered dispenser as an individual-dose drug form. They are readily soluble in cold water, a clear solution resulting.

We claim:

1. A formulation that comprises (i) a sparingly water-soluble active agent that is in non-crystalline form and (ii) a hydrophilic peptide having a molecular weight over 100 daltons, wherein the presence of said hydrophilic peptide allows for said sparingly water-soluble active agent to remain in dispersed form at the molecular and ionic level.

2. The formulation of claim 1, wherein said hydrophilic peptide is a collagen or gelatin.

3. The formulation of claim 1, wherein said hydrophilic peptide is a sol/gel-forming agent.

4. The formulation of claim 2, wherein said collagen is a collagen hydrolyzate.

5. The formulation of claim 2, wherein said gelatin is a fractionated gelatin.

6. The formulation of claim 4, wherein said hydrophilic peptide has an average maximum molecular weight of $9.5 \times 10^4$ daltons.

7. The formulation of claim 4, wherein said hydrophilic peptide is an elastin hydrolyzate.

8. The formulation of claim 1, wherein said hydrophilic peptide is a plant protein or plant protein hydrolyzate.

9. The formulation of claim 1, wherein the weight ratio of said sparingly water-soluble active agent to said hydrophilic peptide ranges from 1.0:0.5 to 1:100.

10. The formulation of claim 1, which further comprises another hydrophilic macromolecule which is selected from the group consisting of agar-agar, gum arabic, pectin, tragacanth, xanthan, naturally occurring starch, modified starch, dextran, dextrin, maltodextrin, chitosan, alginate, polyvinyl alcohol, polyvinyl pyrrolidone, polyethylene glycol, polyacrylic acid polymer, methacrylic acid ester polymer, and mixtures thereof.

11. The formulation of claim 1, which further comprises a pharmaceutically acceptable carrier or excipient.

12. The formulation of claim 1, which further comprises an additional compound selected from the group consisting of glycerol, propylene glycol, polyethylene glycol, triacetin, sorbitol, sorbitan, glucose, polyol, sugar alcohol and mixtures thereof.

13. The formulation of claim 12, wherein the weight ratio of said additional compound to said hydrophilic peptide ranges from 1:0.001 to 1:50.

14. The formulation of claim 1, which is in tablet form.

15. A process for producing a formulation according to claim 1, which comprises:

(i) suspending or dissolving a sparingly water-soluble active compound in at least one solvent;

(ii) mixing the resultant suspension or solution with a hydrophilic peptide having a molecular weight over 100 daltons; and (iii) removing all or part of said at least one solvent, thereby producing a formulation according to claim 1.

16. The process of claim 15, wherein said at least one solvent is a water-miscible organic solvent selected from the group consisting of an alcohol, a ketone, an ether, an ester, and mixtures thereof.

17. The process of claim 15, wherein said at least one solvent is selected from the group consisting of methanol, ethanol, isopropanol, glycerol, polyethylene glycol, 1,2-propylene glycol, and mixtures thereof.

18. The process of claim 15, wherein said at least one solvent modifies the hydrated shell of said hydrophilic peptide.

19. The process of claim 15, wherein step (i) results in the formation of a salt.

20. The process of claim 19, wherein said salt formation is reversed in step (ii).

21. The process of claim 15, which is conducted under an inert gas atmosphere.

22. The process of claim 21, wherein said insert gas is nitrogen or argon.

23. The process of claim 15, wherein said solvent is a volatile water-miscible organic solvent.

24. The process of claim 15, wherein all of said at least one solvent is removed in step (iii).

25. The process of claim 15, which further includes a spray drying step.

26. The process of claim 15, which further includes a freeze drying step.

27. The process of claim 26, wherein the formulation is shaped in the form of cryopellets prior to freeze drying.

28. The process of claim 15, wherein in step (ii), an additional hydrophilic macromolecule selected from the group consisting of agar-agar, gum arabic, pectin, traganth, xanthan, naturally occurring starch, modified starch, dextran, dextrin, maltodextrin, chitosan, alginate, polyvinyl alcohol, polyvinyl pyrrolidone, polyethylene glycol, polyacrylic acid, methacrylic acid polymer, methacrylic acid ester polymer, and mixtures thereof is added to said formulation.

29. The process of claim 28, wherein the weight ratio of said additional hydrophilic macromolecule to said hydrophilic peptide is at most 1:1.

30. The process of claim 15, which further includes the addition of a pharmaceutically acceptable carrier or excipient.

31. The process of claim 15, wherein said hydrophilic peptide is a gelatin or fractionated gelatin having an average maximum molecular weight of $9.5 \times 10^4$ daltons.

32. The process of claim 27, wherein said cryopellets are shaped from the mixture that results upon combination of said sparingly water-soluble active agent, hydrophilic peptide, and an additional compound selected from the group consisting of glycerol, propylene glycol, polyethylene glycol, triacetin, sorbitol, sorbitan, glucose, polyol, sugar alcohol and mixtures thereof by dropwise addition of said mixture into liquid nitrogen.

33. The process of claim 15, wherein said hydrophilic peptide has an ash content below 2% by weight.

34. The process of claim 15, wherein said hydrophilic peptide has an ash content below 0.2%.

35. The process of claim 34, wherein a calcium or magnesium salt is added during step (ii).

36. A pharmaceutically acceptable composition comprising the formulation of claim 1.

37. The formulation of claim 36, wherein said hydrophilic peptide is a sol/gel forming agent.

38. A formulation according to claim 36 which further comprises at least one additional hydrophilic macromolecule selected from the group consisting of agar-agar, gum arabic, pectin, tragacanth, xanthan, naturally occurring starch, modified starch, dextran, dextrin, maltodextrin, chitosan, alginate, polyvinyl alcohol, polyvinyl pyrrolidone, polyethylene glycol, polyacrylic acid, methacrylic acid polymer, methacrylic acid ester polymer, and mixtures thereof.

39. The formation of claim 9, which is in the form of a tablet.

40. The process of claim 15, wherein at least one solvent modifies the hydrated shell of said hydrophilic peptide.

41. The process of claim 15, wherein dissolution of said sparingly water-soluble active agent results in the formation of a salt.

42. The process of claim 41, wherein said salt formation is effected in the presence of ammonia.

43. The process of claim 42, which is effected under an inert gas.

44. The process of claim 15, which includes removal of at least one volatile water-miscible solvent.

45. The process of claim 44, wherein said removal is effected before or during step (iii).

46. The process of claim 27, which includes the addition of another hydrophilic macromolecule selected from the group consisting of agar-agar, gum arabic, pectin, tragacanth, xanthan, a naturally occurring starch, a modified starch, dextran, dextrin, maltodextrin, chitosan, alginate, polyvinyl alcohol, polyvinyl pyrrolidone, polyethylene glycol, polyacrylic acid, methacrylic acid polymer, methacrylic acid ester polymer, and mixtures thereof.

47. The process of claim 15, wherein said hydrophilic peptide is a gelatin or fractionated gelatin having an average maximum molecular weight of $9.5 \times 10^4$ daltons, and the process further includes the addition of a pharmaceutically acceptable carrier or excipient.

48. The process of claim 47, which further includes the addition of at least one other compound selected from the group consisting of agar-agar, gum arabic, pectin, tragacanth, xanthan, naturally occurring starch, modified starch, dextran, dextrin, maltodextrin, chitosan, alginate, polyvinyl alcohol, polyvinyl pyrrolidone, polyethylene glycol, polyacrylic acid polymer, methacrylic acid ester polymer, and mixtures thereof.

49. The process as claimed in claim 32, wherein said hydrophilic peptide has an ash content below 2%.

50. The formulation of claim 1, wherein the weight ratio of said sparingly water-soluble active agent to said hydrophilic peptide ranges from 1:2 to 1:50.

* * * * *